(12) United States Patent
Okamoto et al.

(10) Patent No.: US 10,067,207 B2
(45) Date of Patent: Sep. 4, 2018

(54) PET-MRI APPARATUS

(71) Applicant: Toshiba Medical Systems Corporation, Otawara-shi (JP)

(72) Inventors: Kazuya Okamoto, Saitama (JP); Takuzo Takayama, Utsunomiya (JP); Hitoshi Yamagata, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 659 days.

(21) Appl. No.: 14/522,024

(22) Filed: Oct. 23, 2014

(65) Prior Publication Data

US 2015/0045653 A1  Feb. 12, 2015

Related U.S. Application Data

(63) Continuation of application No. PCT/JP2013/062131, filed on Apr. 24, 2013.

(30) Foreign Application Priority Data

Apr. 24, 2012  (JP) .................. 2012-099058

(51) Int. Cl.
*A61B 5/055* (2006.01)
*G01R 33/48* (2006.01)
(Continued)

(52) U.S. Cl.
CPC .......... *G01R 33/481* (2013.01); *A61B 5/0035* (2013.01); *A61B 5/055* (2013.01);
(Continued)

(58) Field of Classification Search
CPC .. G01R 33/481; G01R 33/307; G01R 33/385; A61B 6/037; A61B 5/0035; A61B 5/055; A61B 5/0555; G01T 1/1603
(Continued)

(56) References Cited

U.S. PATENT DOCUMENTS 8,295,905 B2  10/2012  Graves et al.
8,547,100 B2  10/2013  Solf et al.
(Continued)

FOREIGN PATENT DOCUMENTS

JP  2004-350942 A  12/2004
JP  2008-525161 A  7/2008
(Continued)

OTHER PUBLICATIONS

U.S. Appl. No. 14/522,228, filed Oct. 23, 2014, Yamagata, et al.
(Continued)

*Primary Examiner* — Sanjay Cattungal
(74) *Attorney, Agent, or Firm* — Oblon, McClelland, Maier & Neustadt, L.L.P.

(57) ABSTRACT

A positron emission tomography (PET)-magnetic resonance imaging (MRI) apparatus according to an embodiment includes a gantry having a static magnetic field magnet, a gradient coil, and a radio frequency coil, a PET detector, and a moving mechanism. The static magnetic field magnet generates a static magnetic field in a bore having an approximately cylindrical shape. The gradient coil is disposed on an inner circumference side of the static magnetic field magnet and applies a gradient magnetic field to an object disposed in the bore. The radio frequency coil is disposed on an inner circumference side of the gradient coil and applies a radio frequency magnetic field to the object. The PET detector detects gamma rays emitted from a positron-emitting radionuclide injected into the object. The moving mechanism causes the PET detector in the gantry along the axial direction of the bore.

11 Claims, 11 Drawing Sheets

(51) Int. Cl.
*G01T 1/16* (2006.01)
*A61B 5/00* (2006.01)
*A61B 6/03* (2006.01)
*G01R 33/30* (2006.01)
*G01R 33/385* (2006.01)

(52) U.S. Cl.
CPC ............ *A61B 6/037* (2013.01); *G01R 33/307* (2013.01); *G01R 33/385* (2013.01); *G01T 1/1603* (2013.01); *A61B 5/0555* (2013.01)

(58) Field of Classification Search
USPC .................................................. 600/407–430
See application file for complete search history.

(56) References Cited

U.S. PATENT DOCUMENTS

| | | | |
|---|---|---|---|
| 9,386,941 B2* | 7/2016 | Piferi | |
| 2003/0179853 A1* | 9/2003 | Amemiya | A61B 6/037 378/63 |
| 2004/0120467 A1* | 6/2004 | Wollenweber | A61B 6/04 378/206 |
| 2004/0195512 A1* | 10/2004 | Crosetto | A61B 6/037 250/363.04 |
| 2007/0102641 A1 | 5/2007 | Schmand et al. | |
| 2007/0143921 A1* | 6/2007 | Hiyama | A61B 5/0555 5/601 |
| 2008/0028526 A1* | 2/2008 | Kato | A61B 5/0555 5/601 |
| 2008/0146914 A1 | 6/2008 | Polzin et al. | |
| 2008/0230704 A1* | 9/2008 | Daghighian | A61B 6/037 250/363.03 |
| 2008/0267358 A1* | 10/2008 | Hiyama | A61B 5/0555 378/209 |
| 2009/0221903 A1 | 9/2009 | Corbeil et al. | |
| 2010/0087730 A1* | 4/2010 | Yamada | A61B 5/055 600/419 |
| 2010/0219828 A1* | 9/2010 | Takahashi | A61B 5/0555 324/309 |
| 2011/0079723 A1* | 4/2011 | Gagnon | A61B 6/037 250/362 |
| 2011/0224534 A1* | 9/2011 | Yamaya | G01R 33/481 600/411 |
| 2011/0251480 A1 | 10/2011 | Graves et al. | |
| 2013/0030287 A1* | 1/2013 | Yamaya | A61B 6/037 600/425 |
| 2013/0234710 A1 | 9/2013 | Kanno et al. | |
| 2013/0241555 A1* | 9/2013 | Obata | A61B 6/037 324/318 |
| 2013/0296689 A1 | 11/2013 | Okamoto et al. | |
| 2013/0324836 A1 | 12/2013 | Yamaya et al. | |
| 2014/0135613 A1 | 5/2014 | Yamaya et al. | |

FOREIGN PATENT DOCUMENTS

| | | |
|---|---|---|
| JP | 2009-540882 A | 11/2009 |
| JP | 2011-30682 A | 2/2011 |
| JP | 2011-514518 A | 5/2011 |
| JP | 2011-185796 A | 9/2011 |
| JP | 2012-152551 A | 8/2012 |
| KR | 10-2008-0105442 | 12/2008 |
| KR | 10-2008-0105443 | 12/2008 |

OTHER PUBLICATIONS

U.S. Appl. No. 13/938,592, filed Jul. 10, 2013, 2013-0324836, Yamaya et al.
U.S. Appl. No. 13/935,812, filed Jul. 5, 2013, 2013-0296689, Okamoto et al.
U.S. Appl. No. 13/873,706, filed Apr. 30, 2013, 2013-0234710, Kanno et al.
U.S. Appl. No. 13/874,795, filed May 1, 2013, 2013-0241555, Obata et al.
U.S. Appl. No. 14/452,580, filed Aug. 6, 2014, Takayama et al.
U.S. Appl. No. 14/450,697, filed Aug. 4, 2014, Takayama et al.
International Search Report dated Jun. 18, 2013 for PCT/JP2013/062131 filed on Apr. 24, 2013 with English Translation.
International Written Opinion dated Jun. 18, 2013 for PCT/JP2013/062131 filed on Apr. 24, 2013.
Extended Search Report dated Jan. 20, 2016 in European Patent Application No. 13781234.3.

* cited by examiner

PET-MRI APPARATUS

CROSS-REFERENCE TO RELATED APPLICATIONS

This application is a continuation of PCT international application Ser. No. PCT/JP2013/062131 filed on Apr. 24, 2013 which designates the United States, the entire contents of which are incorporated herein by reference.

FIELD

Embodiments relate to a positron emission tomography (PET)-magnetic resonance imaging (MRI) apparatus.

BACKGROUND

In recent years, PET-MRI apparatuses having a combination of positron emission tomography (PET) apparatuses and magnetic resonance imaging (MRI) apparatuses have been made into products. Generally, the PET-MRI apparatuses are realized by attaching PET detectors to the MRI apparatuses, and in many cases, the positions of the PET detectors are fixed. However, when the PET detectors are fixed in the vicinity of magnetic field centers of the MRI apparatuses, the PET detectors may interfere with high power radio frequency (RF) magnetic fields generated in the magnetic field centers and radio frequency coils (RF coils) detecting generated magnetic resonance signals, which may cause data acquisition not to be properly made.

DETAILED DESCRIPTION

A positron emission tomography (PET)-magnetic resonance imaging (MRI) apparatus according to the present embodiment comprises a static magnetic field magnet, a gradient coil, a radio frequency coil, a PET detector and a moving mechanism. The static magnetic field magnet generates a static magnetic field in a bore having an approximately cylindrical shape. The gradient coil is disposed on an inner circumference side of the static magnetic field magnet and applies a gradient magnetic field to an object disposed in the bore. The radio frequency coil is disposed on an inner circumference side of the gradient coil and applies a radio frequency magnetic field to the object. The PET detector detects gamma rays emitted from a positron-emitting radionuclide injected into the object. The moving mechanism causes the PET detector to move in the gantry along the axial direction of the bore.

Embodiments of a PET-MRI apparatus are described below with reference to the accompanying drawings.

First Embodiment

Figure 1:
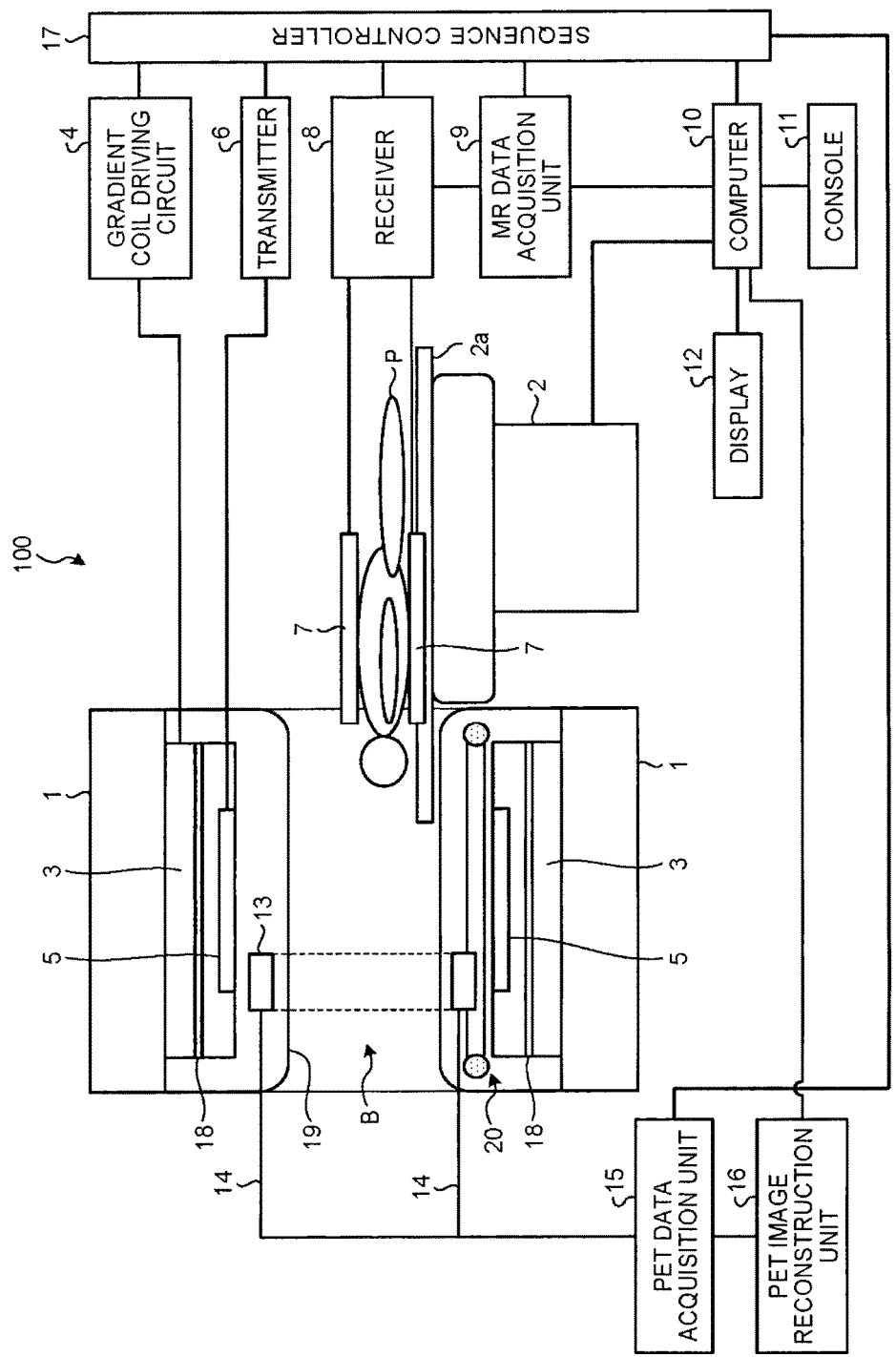
FIG. 1 is a schematic diagram illustrating the overall structure of a PET-MRI apparatus according to a first embodiment.

FIG. 1 is a schematic diagram illustrating the overall structure of a PET-MRI apparatus according to a first embodiment. As illustrated in FIG. 1, a PET-MRI apparatus 100 according to the first embodiment includes a static magnetic field magnet 1, a couch 2, a gradient coil 3, a gradient coil driving circuit 4, a transmitting radio frequency coil 5, a transmitter 6, a receiving radio frequency coil 7, a receiver 8, an MR data acquisition unit 9, a computer (a position detection unit) 10, a console 11, a display 12, a PET detector 13, signal lines 14, a PET data acquisition unit 15, a PET image reconstruction unit 16, a sequence controller 17, a radio frequency shield 18, and a bore cover 19.

The static magnetic field magnet 1 generates a static magnetic field in a bore B having an approximately cylindrical shape. The couch 2 has a couchtop 2a on which an object P is placed. When the object P is imaged, the couch 2 causes the couchtop 2a to move into the bore B with the longitudinal direction of the couchtop 2a being along the axial direction of the bore B, thereby moving the object P into the static magnetic field.

The gradient coil 3 applies gradient magnetic fields Gx, Gy, and Gz on the object P. The magnetic field intensities of the gradient magnetic fields Gx, Gy, and Gz change linearly in the X, Y, and Z directions, respectively. The gradient coil 3 is formed in an approximately cylindrical shape and disposed on an inner circumference side of the static magnetic field magnet 1. The gradient coil driving circuit 4 drives the gradient coil 3 under control of the sequence controller 17.

The transmitting radio frequency coil 5 applies a radio frequency magnetic field on the object P placed in the static magnetic field on the basis of a radio frequency pulse transmitted from the transmitter 6. The transmitting radio frequency coil 5 is formed in an approximately cylindrical shape and disposed on an inner circumference side of the gradient coil 3. The transmitter 6 transmits the radio frequency pulse to the transmitting radio frequency coil 5 under control of the sequence controller 17.

The receiving radio frequency coil 7 detects a magnetic resonance signal emitted from the object P due to the application of the radio frequency magnetic field and the gradient magnetic field. For example, the receiving radio frequency coil 7 is a surface coil disposed on the surface of the object P depending on a portion to be imaged. For example, when a body portion of the object P is imaged, two receiving radio frequency coils 7 are disposed on the upper part and the lower part of the object P. The receiver 8 receives the magnetic resonance signal detected by the receiving radio frequency coil 7 and sends the received magnetic resonance signal to the MR data acquisition unit 9, under control of the sequence controller 17.

The MR data acquisition unit 9 acquires the magnetic resonance signal sent from the receiver 8, under control of the sequence controller 17. The MR data acquisition unit 9 amplifies the acquired magnetic resonance signal and performs detection on the amplified signal. Thereafter, the MR data acquisition unit 9 A/D-converts the signal after the detection and sends the converted signal to the computer 10. The computer 10, which is controlled by the console 11, reconstructs an MR image on the basis of the magnetic resonance signal sent from the MR data acquisition unit 9. The computer 10 causes the display 12 to display the reconstructed MR image.

The PET detector 13 detects, as counting information, gamma rays (including annihilation radiation) emitted from positron-emitting radionuclides injected into the object P. The PET detector 13 is formed in a ring shape and disposed on an inner circumference side of the transmitting radio frequency coil 5. For example, the PET detector 13 is formed by arranging detector modules including scintillators and photodetectors in a ring shape. Examples of the scintillator include lutetium yttrium oxyorthosilicate (LYSO), lutetium oxyorthosilicate (LSO), and lutetium gadolinium oxyorthosilicate (LGSO). The photodetector is, for example, a semiconductor detector such as an avalanche photodiode (APD) element or a SiPM (Silicon Photomultiplier), or a photomultiplier tube (PMT). The PET detector 13 sends the detected counting information to the PET data acquisition unit 15 through the signal lines 14.

The PET data acquisition unit 15 produces simultaneous counting information under control of the sequence controller 17. The PET data acquisition unit 15 produces, as the simultaneous counting information, a combination of counting information of gamma rays that are emitted from the positron-emitting radionuclides and approximately simultaneously detected, using the counting information of the gamma rays detected by the PET detector 13.

The PET image reconstruction unit 16 reconstructs a PET image using the simultaneous counting information produced by the PET data acquisition unit 15 as projection data. The PET image reconstructed by the PET image reconstruction unit 16 is transmitted to the computer 10 and displayed on the display 12. The sequence controller 17 receives, from the computer 10, information on various types of imaging sequences executed when the object is imaged and controls the above-described components.

The radio frequency shield 18 is disposed between the gradient coil 3 and the transmitting radio frequency coil 5 and shields the radio frequency magnetic field generated by the transmitting radio frequency coil 5. The bore cover 19 is a cover covering an inner circumference side of the transmitting radio frequency coil 5. The bore cover 19 forms the bore B, which is a space having an approximately cylindrical shape, inside an approximately cylindrical structure composed of the static magnetic field magnet 1, the gradient coil 3, the radio frequency shield 18, and the transmitting radio frequency coil 5.

The PET-MRI apparatus 100 according to the first embodiment further includes a moving mechanism 20 that causes the PET detector 13 to move along the axial direction of the bore, in addition to the above-described structure.

Figure 2:
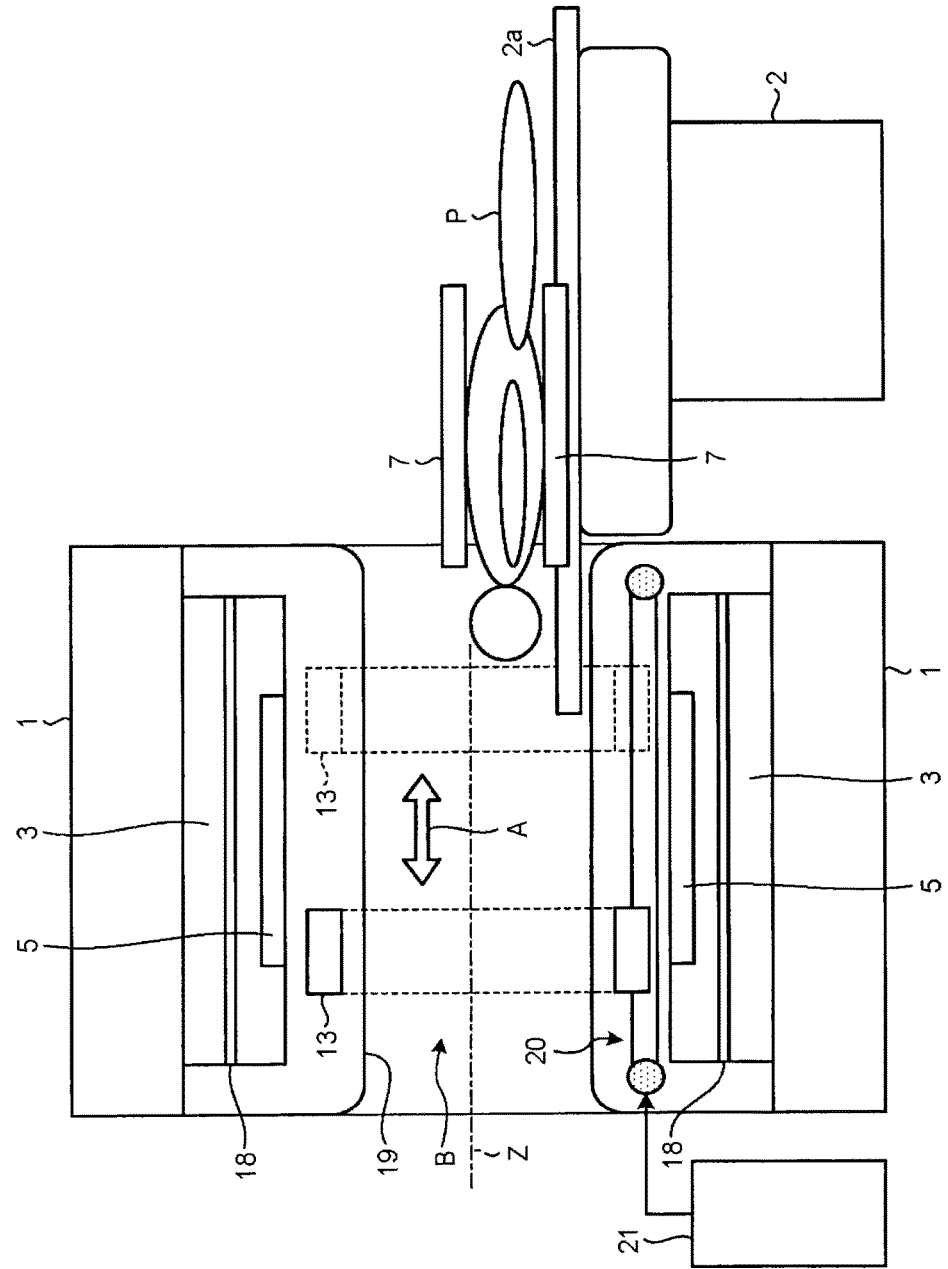
FIG. 2 is a schematic diagram illustrating an example of the moving mechanism of a PET detector according to the first embodiment.

FIG. 2 is a schematic diagram illustrating an example of the moving mechanism of a PET detector according to the first embodiment. As illustrated in FIG. 2, in the first embodiment, the PET detector 13 is disposed between the transmitting radio frequency coil 5 and the bore cover 19. The moving mechanism 20 is also disposed between the transmitting radio frequency coil 5 and the bore cover 19.

As illustrated in FIG. 2, the moving mechanism 20 causes the PET detector 13 to move in a gantry along the axial direction of the bore. For example, the moving mechanism 20 causes the PET detector 13 to move, in a space formed between the transmitting radio frequency coil 5 and the bore cover 19, in the Z-axis direction of the bore B (in a direction indicated by the double-headed arrow A illustrated in FIG. 2). The moving mechanism 20 causes the PET detector 13 to move by being driven by a driving device 21, for example.

For example, the moving mechanism 20 is composed of at least two rotational shafts disposed along the axial direction of the bore B at the ends of the gantry including the static magnetic field magnet 1, the gradient coil 3, the transmitting radio frequency coil 5, and the bore cover 19, and a belt wound between the rotational shafts. The driving device 21 rotationally drives the rotational shafts, so that the PET detector 13 fixed to a part of the belt is moved in the Z-axis direction of the bore B.

The PET-MRI apparatus according to the first embodiment is described as above. In the PET-MRI apparatuses having been made into products in recent years, the positions of the PET detectors are fixed in many cases. In some of the PET-MRI apparatuses, the PET detectors are removable. Even in such cases, the positions of most of the PET detectors are fixed. Although PET-MRI apparatuses have been also developed in which two PET detectors are disposed spaced apart from each other, the PET detectors need not always be disposed around the imaging center and may be allowed to be somewhat off the imaging center.

In fact, if the PET detectors and the radio frequency coil are in different positions in the axial direction of the bore, it would be more preferable for data acquisition, as interference would become smaller. Although imaging by the MRI can be performed only at the central position in the axial direction of the bore, imaging by the PET is executable at any position in the axial direction of the bore. Since the imaging by the MRI and the imaging by the PET differ from each other in data acquisition time, that the position of the object in PET imaging is always the center of the magnetic field is in some cases inconvenient for constructing an imaging protocol combining MRI imaging and PET imaging.

In contrast, in the PET-MRI apparatus 100 according to the first embodiment, the PET detector 13 is caused to move in the axial direction of the bore by the moving mechanism 20, and thereby the PET detector 13 can be moved to a position distant from the magnetic field center. As a result, effect of interference between the PET detector and the magnetic field on data acquisition can be lessened. In addition, a degree of freedom in establishing the imaging protocol in a combination of MRI and PET can be increased.

The moving mechanism of the PET detector is not limited to the example illustrated in FIG. 2. Other examples of the moving mechanism are described below as second to eighth embodiments.

Second Embodiment

Figure 3:
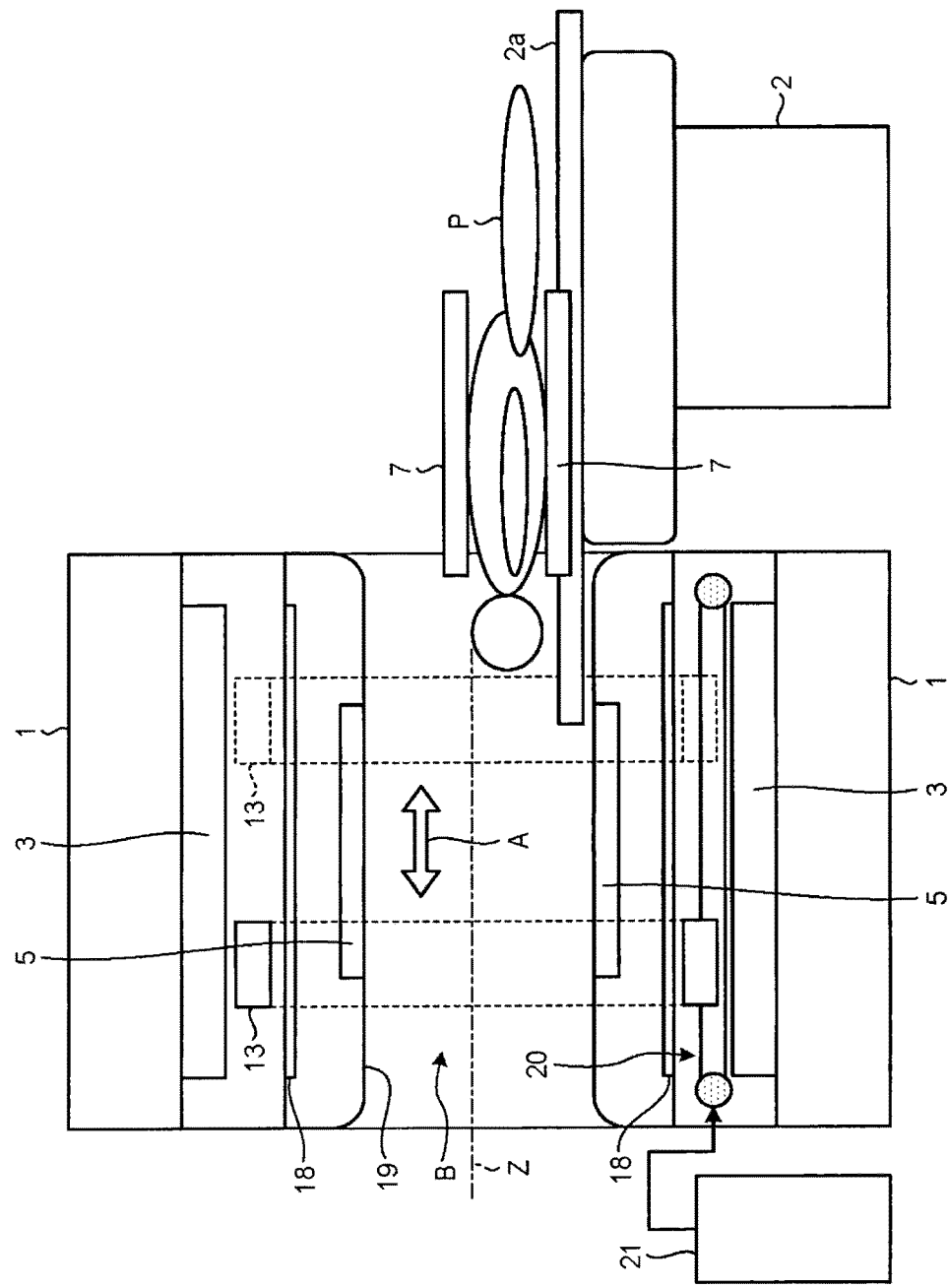
FIG. 3 is a schematic diagram illustrating an example of the moving mechanism of a PET detector according to a second embodiment.

FIG. 3 is a schematic diagram illustrating an example of the moving mechanism of a PET detector according to a second embodiment. As illustrated in FIG. 3, in the second embodiment, the PET detector 13 is disposed between the gradient coil 3 and the radio frequency shield 18. The moving mechanism 20 is also disposed between the gradient coil 3 and the radio frequency shield 18. As illustrated in FIG. 3, the moving mechanism 20 causes the PET detector 13 to move in the gantry along the axial direction of the bore. For example, the moving mechanism 20, by being driven by the driving device 21, causes the PET detector 13 to move in a space formed between the gradient coil 3 and the radio frequency shield 18 in the Z-axis direction of the bore (in a direction indicated by the double-headed arrow A illustrated in FIG. 3).

Third Embodiment

Figure 4:
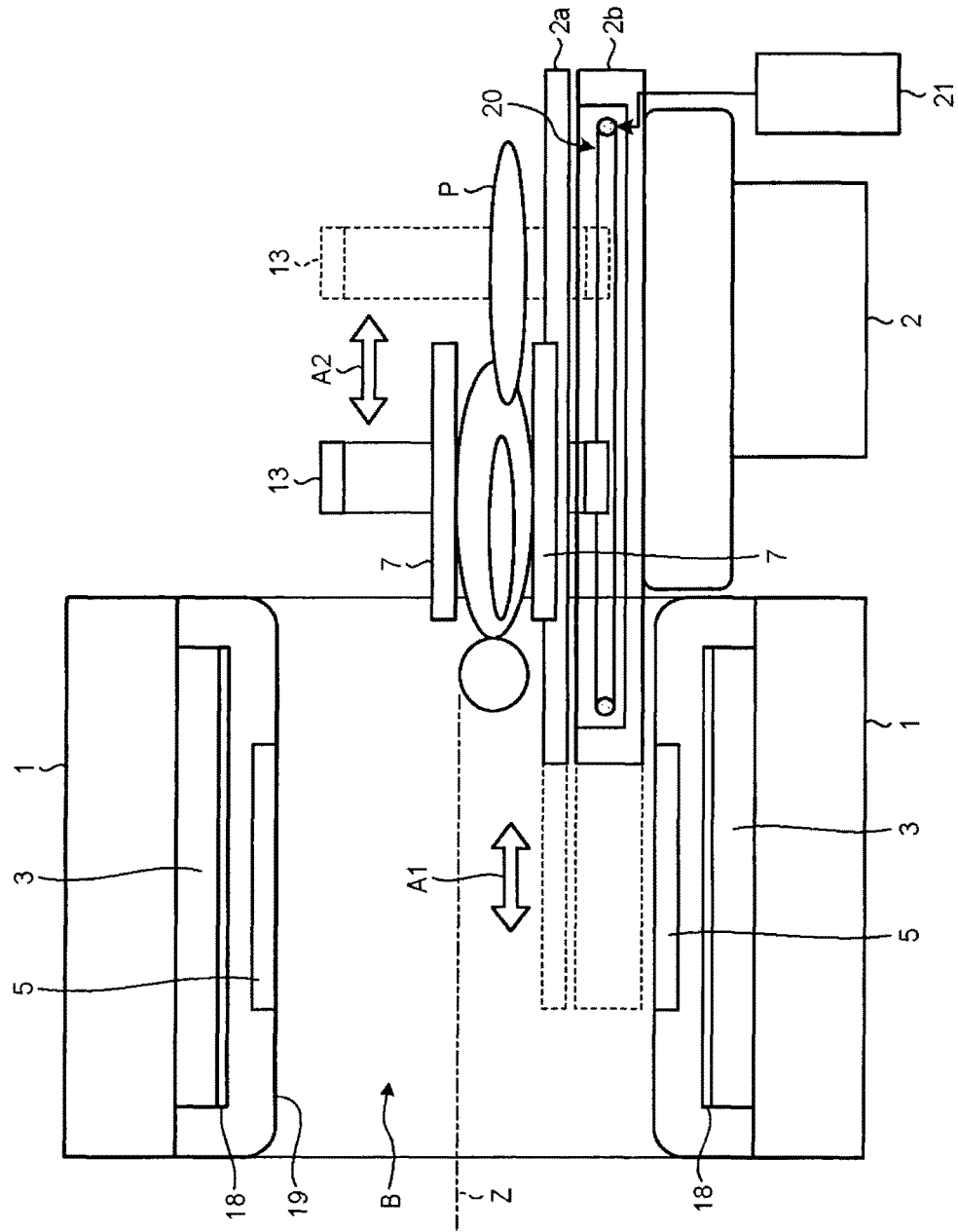
FIG. 4 is a schematic diagram illustrating an example of the moving mechanism of a PET detector according to a third embodiment.

FIG. 4 is a schematic diagram illustrating an example of the moving mechanism of a PET detector according to a third embodiment. As illustrated in FIG. 4, in the third embodiment, the couchtop is divided into the couchtop 2a on which the object P is placed and a couchtop 2b that supports the couchtop 2a from the lower side of the couchtop 2a. The couchtop 2a is placed on the couchtop 2b such that the position of the couchtop 2a relative to the couchtop 2b is not changed. The couch 2 causes the couchtop 2b to move into the bore B while the couchtop 2a is placed on the couchtop 2b (in a direction indicated by the double-headed arrow A1 illustrated in FIG. 4).

The PET detector 13 is provided to the couchtop such that it is movable in the longitudinal direction of the couchtop. For example, the PET detector 13 is disposed to a groove formed on the couchtop 2b along the longitudinal direction of the couchtop 2b, and supported such that it is movable in the longitudinal direction of the couchtop 2b. The moving mechanism 20 is provided in the couchtop. For example, the moving mechanism 20 is driven by the driving device 21 and causes the PET detector 13 to move in the longitudinal direction of the couchtop 2b (in a direction indicated by the double-headed arrow A2 illustrated in FIG. 4).

That is, in the third embodiment, it is also possible to cause the PET detector 13 to move in the Z-axis direction of the bore B along with the movement of the couchtop 2b, and it is also possible to cause the PET detector 13 to move in the Z-axis direction of the bore B along the longitudinal direction of the couchtop 2b even if the position of the couchtop 2b is fixed. The PET detector 13 may be provided to the couchtop 2b in a detachable manner. In such a case, a connector connecting a control line and a power source line of the PET detector 13 is disposed to the couchtop 2b, for example.

Fourth Embodiment

Figure 5:
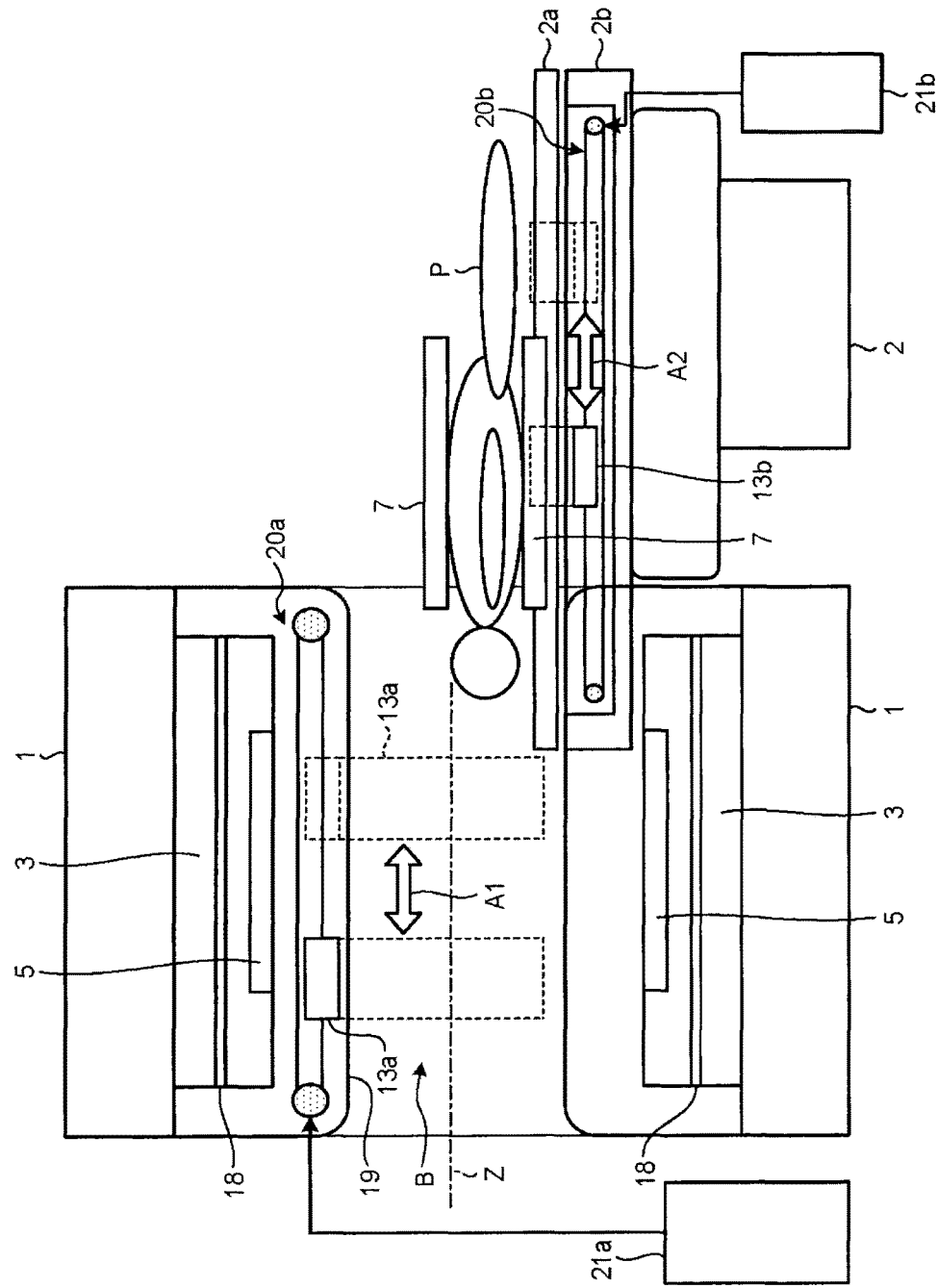
FIG. 5 is a first schematic diagram illustrating an example of the moving mechanism of a PET detector according to a fourth embodiment.
Figure 6:
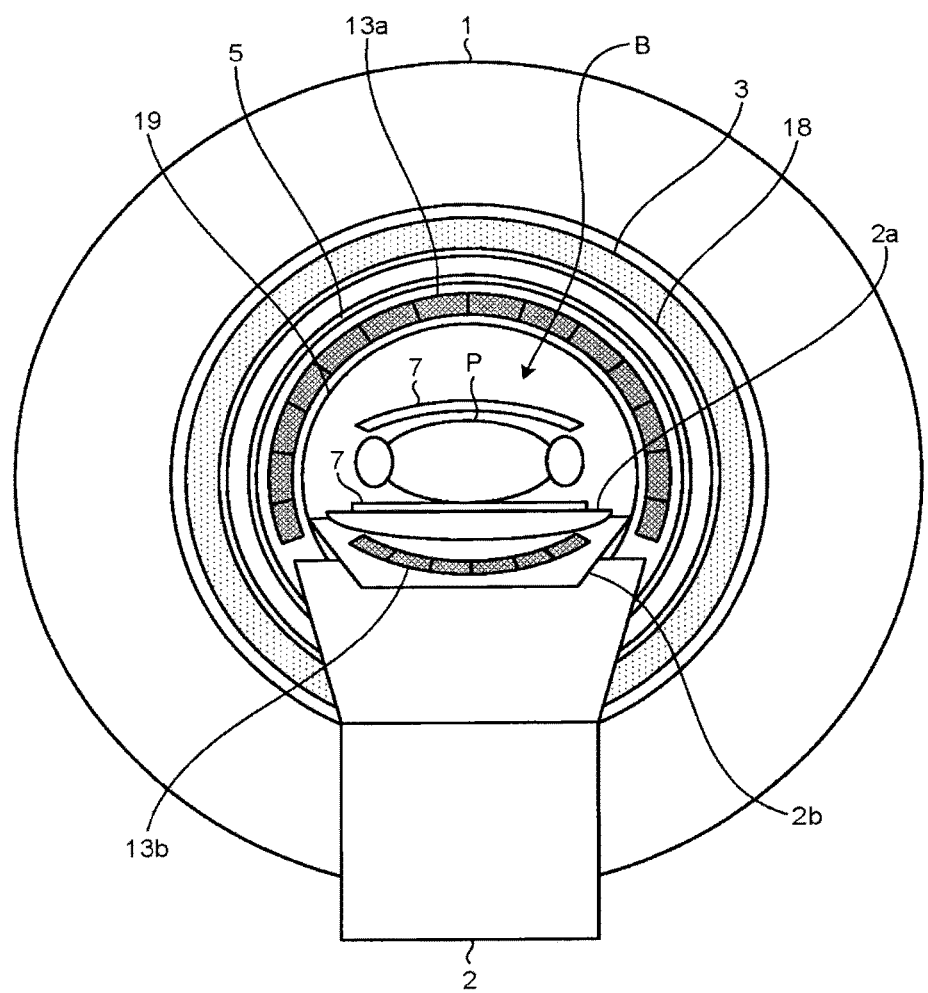
FIG. 6 is a second schematic diagram illustrating the example of the moving mechanism of the PET detector according to the fourth embodiment.

FIGS. 5 and 6 are schematic diagrams illustrating an example of the moving mechanism of a PET detector according to a fourth embodiment. As illustrated in FIG. 5, in the fourth embodiment, the couchtop is divided into the couchtop 2a on which the object P is placed and the couchtop 2b on which the couchtop 2a is placed, in the same manner as the third embodiment. The positional relation between the couchtop 2a and the couchtop 2b, and the operation of the couch 2 are the same as those in the third embodiment.

The PET detector is divided into a first PET detector 13a and a second PET detector 13b. The first PET detector 13a is disposed around the bore B while the second PET detector 13b is disposed to the couchtop. The moving mechanism is also divided into a first moving mechanism 20a and a second moving mechanism 20b. As illustrated in FIG. 5, the first moving mechanism 20a causes the first PET detector 13a to move in the gantry along the axial direction of the bore. For example, the first moving mechanism 20a is driven by a driving device 21a and causes, around the bore B, the first PET detector 13a to move along the Z-axis direction of the bore B (in a direction indicated by the double-headed arrow A1 illustrated in FIG. 5). For example, the second moving mechanism 20b is driven by a driving device 21b and causes the second PET detector 13b to move along the longitudinal direction of the couchtop 2b (in a direction indicated by the double-headed arrow A2 illustrated in FIG. 5).

FIG. 6 illustrates a view of the first PET detector 13a and the second PET detector 13b and their surroundings when viewed from the Z-axis direction of the bore B. As illustrated in FIG. 6, the first PET detector 13a and the second PET detector 13b are each formed in an arc shape. The first PET detector 13a is disposed on the upper side of the bore B such that the inner circumference side of the arc faces the bore B side. The second PET detector 13b is disposed on the couchtop 2b such that the inner circumference side of the arc faces the bore B side.

That is, in the fourth embodiment, the PET detector is divided into the first PET detector 13a provided on the gantry side and the second PET detector 13b provided on the couchtop side, and they can be caused to move independently from each other in the Z-axis direction of the bore B. Data acquisition is performed when the couchtop 2b is inserted in the bore B and the position of the first PET detector 13a and the position of the second PET detector 13b become the same position in the Z-axis direction of the bore B.

The second PET detector 13b may be provided to the couchtop 2b in a detachable manner. In such a case, a connector connecting a control line and a power source line of the second PET detector 13b is disposed to the couchtop 2b, for example. The first PET detector 13a may be controlled such that it cannot move at least in a time period when the object P is inserted.

Fifth Embodiment

Figure 7:
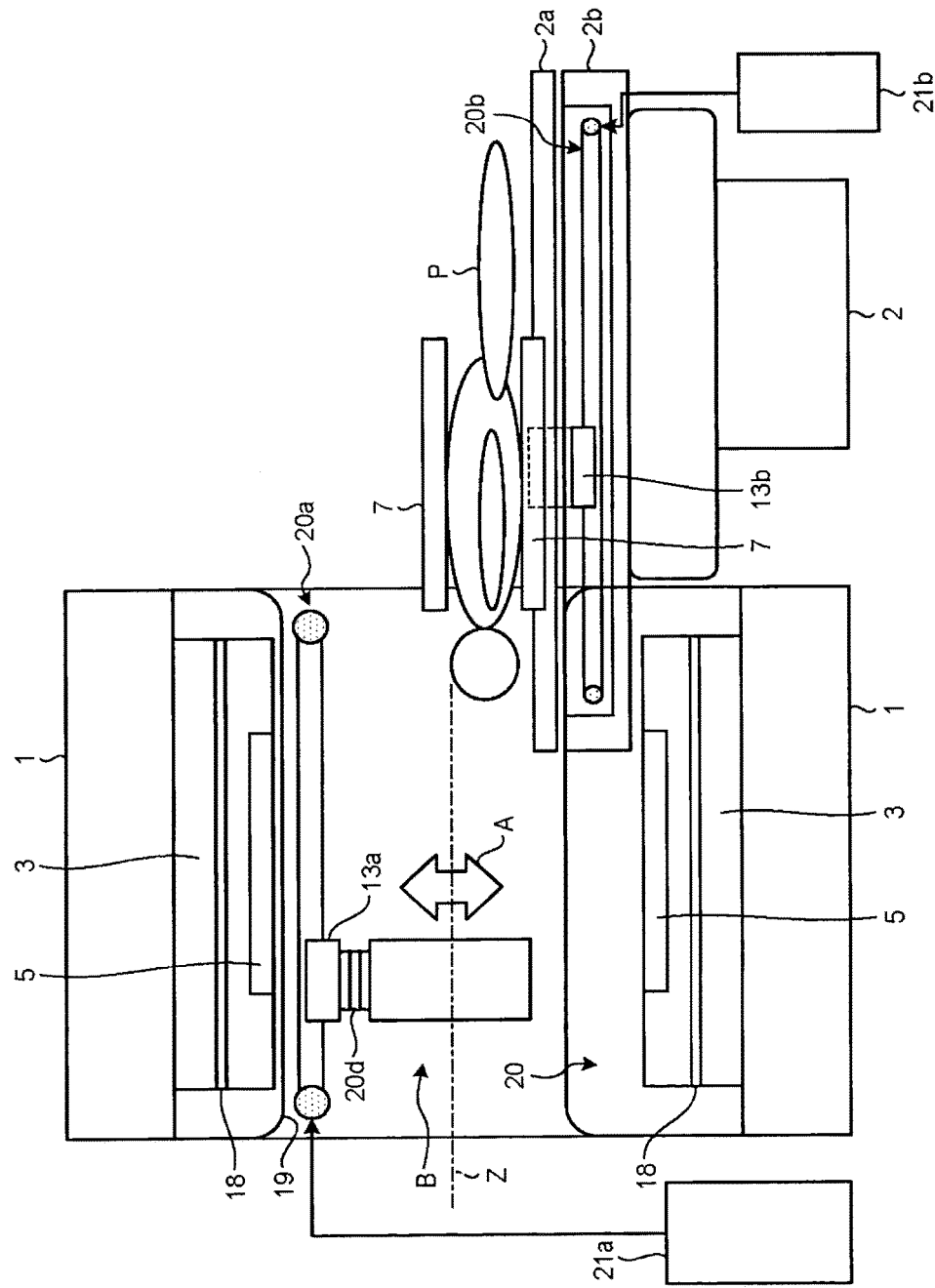
FIG. 7 is a schematic diagram illustrating an example of the moving mechanism of a PET detector according to a fifth embodiment.

FIG. 7 is a schematic diagram illustrating an example of the moving mechanism of a PET detector according to a fifth embodiment. As illustrated in FIG. 7, in the fifth embodiment, the first moving mechanism 20a illustrated in FIG. 5 causes the first PET detector 13a to move additionally in the up-down direction with an up-down moving mechanism 20d (in a direction indicated by the double-headed arrow A illustrated in FIG. 7). As illustrated in FIG. 7, the first moving mechanism 20a also causes the first PET detector 13a to move in the gantry along the axial direction of the bore.

That is, in the fifth embodiment, the first PET detector 13a can be caused to move not only in the Z-axis direction of the bore B but also in the up-down direction. As a result, the distance between the two PET detectors can be adjusted in accordance with the body size of the object P, for example.

Sixth Embodiment

Figure 8:
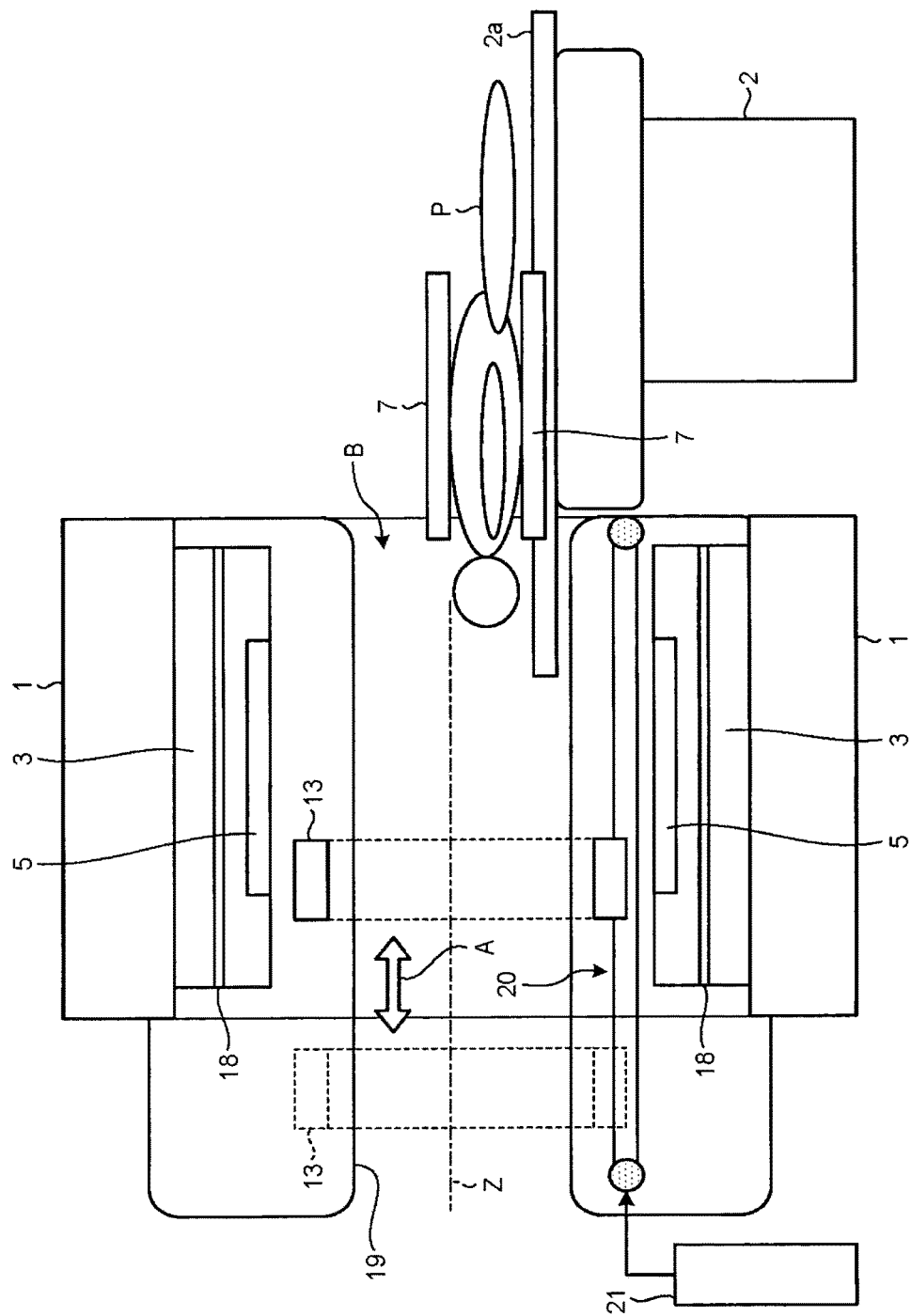
FIG. 8 is a schematic diagram illustrating an example of the moving mechanism of a PET detector according to a sixth embodiment.

FIG. 8 is a schematic diagram illustrating an example of the moving mechanism of a PET detector according to a sixth embodiment. As illustrated in FIG. 8, in the sixth embodiment, the PET detector 13 is provided such that it can move outside the static magnetic field magnet 1. For example, as illustrated in FIG. 8, the bore cover 19 is formed such that it protrudes from the static magnetic field magnet 1 on a side where the couch 2 is not placed.

The moving mechanism 20 is provided such that it extends in a space formed inside the protruding portion of the bore cover 19. The moving mechanism 20 causes the PET detector 13 to move along the Z-axis direction of the bore B (in a direction indicated by the double-headed arrow A illustrated in FIG. 8). In addition, as illustrated in FIG. 8, the moving mechanism 20 causes the PET detector 13 to move in the gantry along the axial direction of the bore. As a result, the moving mechanism 20 causes the PET detector 13 to move inside the portion protruding from the static magnetic field magnet 1 of the bore cover 19, thereby making it possible to move the PET detector 13 outside the static magnetic field magnet 1.

That is, in the sixth embodiment, because the PET detector 13 can be caused to move outside the static magnetic field magnet 1, effect of interference between the first PET detector 13 and the magnetic field on data acquisition can be surely lessened.

Seventh Embodiment

Figure 9:
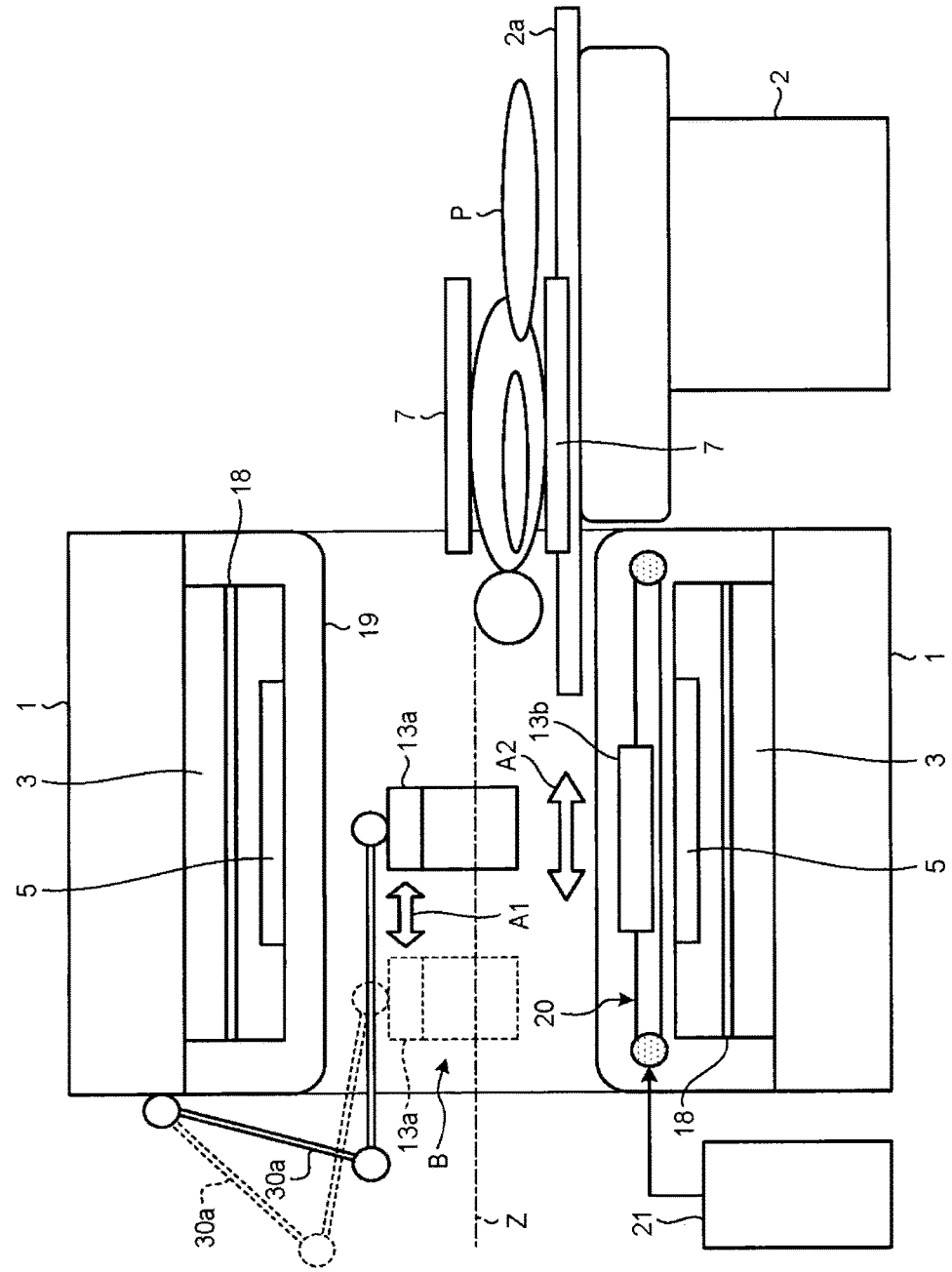
FIG. 9 is a schematic diagram illustrating an example of the moving mechanism of a PET detector according to a seventh embodiment.

FIG. 9 is a schematic diagram illustrating an example of the moving mechanism of a PET detector according to a seventh embodiment. As illustrated in FIG. 9, in the seventh embodiment, the PET detector is divided into the first PET detector 13a and the second PET detector 13b. The first PET detector 13a and the second PET detector 13b are disposed such that they face to each other with respect to the Z-axis of the bore B interposed therebetween.

For example, as illustrated in FIG. 9, a retainer 30a is provided that retains the first PET detector 13a such that the first PET detector 13a is movable in the bore B. As illustrated in FIG. 9, the retainer 30a causes the first PET detector 13a to move in the gantry along the axial direction of the bore. For example, the retainer 30a causes the first PET detector 13a to move along the Z-axis direction of the bore B (in a direction indicated by the double-headed arrow A1 illustrated in FIG. 9). For example, the retainer 30a can be realized using an arm having a plurality of joints. The retainer 30a may cause the first PET detector 13a to move by being driven by a driving device or may cause the first PET detector 13a to move by being manually operated by an operator.

As illustrated in FIG. 9, the moving mechanism 20 causes the second PET detector 13b to move in the gantry along the axial direction of the bore. For example, the moving mechanism 20 causes the second PET detector 13b to move along the Z-axis direction of the bore B in coordination with the movement of the first PET detector 13a (in a direction indicated by the double-headed arrow A2 illustrated in FIG. 9). The second PET detector 13b has a width larger than that of the first PET detector 13a in the Z-axis direction of the bore B. When the width of the second PET detector 13b in the Z-axis direction of the bore B is sufficiently large, the position of the second PET detector 13b may be fixed, thereby making it possible to eliminate the moving mechanism 20.

Eighth Embodiment

Figure 10:
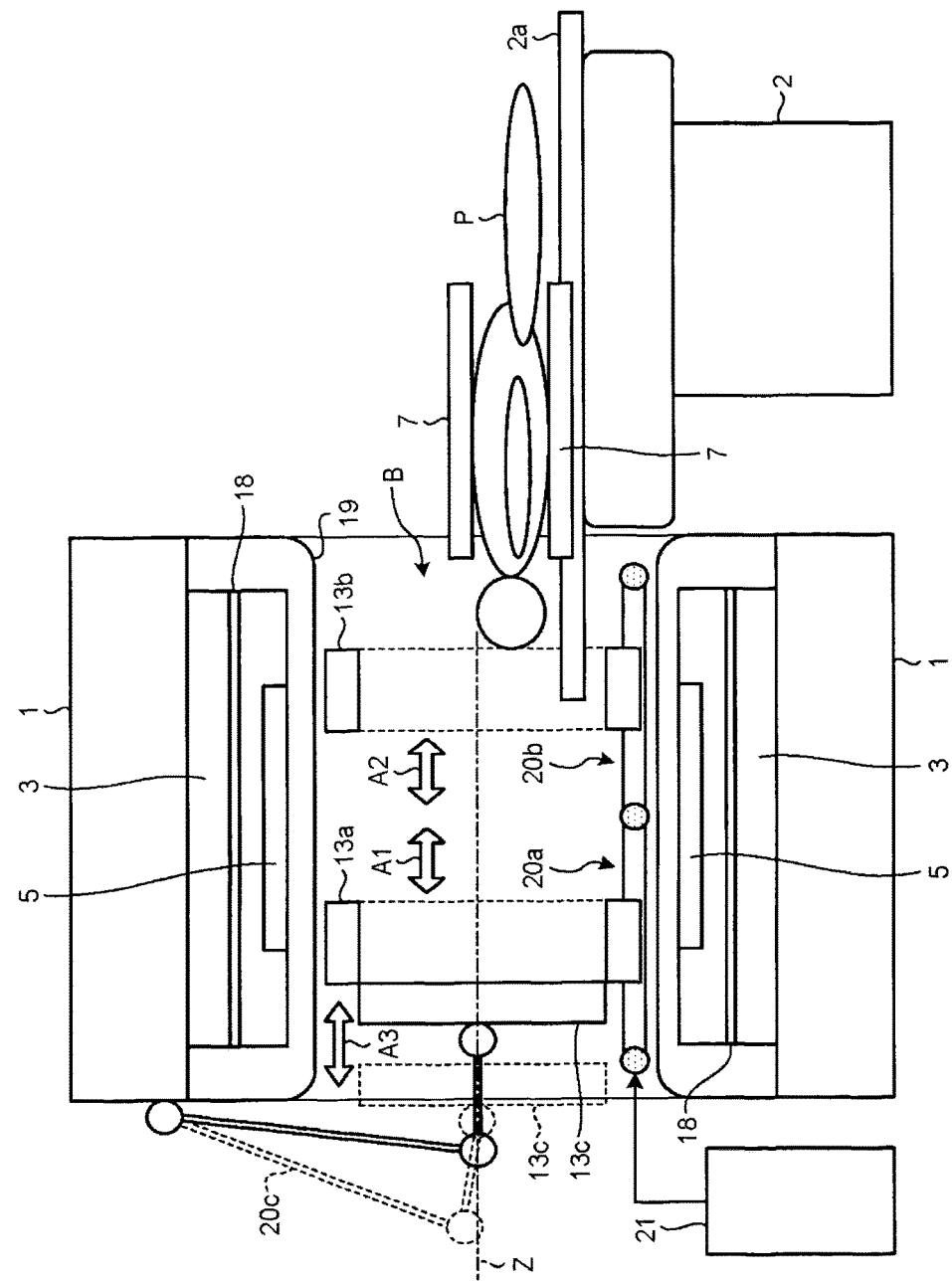
FIG. 10 is a schematic diagram illustrating an example of the moving mechanism of a PET detector according to an eighth embodiment.

FIG. 10 is a schematic diagram illustrating an example of the moving mechanism of a PET detector according to an eighth embodiment. As illustrated in FIG. 10, in the eighth embodiment, included are the first PET detector 13a, the second PET detector 13b, and a PET detector 13c.

The first PET detector 13a and the second PET detector 13b are each formed in a ring shape and each have a detection surface on the inner circumference of the ring. The first PET detector 13a and the second PET detector 13b are disposed side by side along the Z-axis of the bore B. The first PET detector 13a is caused to move in the Z-axis direction of the bore B by the first moving mechanism 20a (in a direction indicated by the double-headed arrow A1 illustrated in FIG. 10) while the second PET detector 13b is caused to move in the Z-axis direction of the bore B by the second moving mechanism 20b (in a direction indicated by the double-headed arrow A2 illustrated in FIG. 10). As illustrated in FIG. 10, the first PET detectors 13a and the second PET detector 13b are caused to move in the gantry by the first moving mechanism 20a and the second moving mechanism 20b. As a result, the distance between the first PET detector 13a and the second PET detector 13b are arbitrarily adjusted.

The PET detector 13c has a detection surface that is approximately perpendicular to the Z-axis direction of the bore B. The PET detector 13c is caused to move along the Z-axis direction of the bore B by a moving mechanism 20c (in a direction indicated by the double-headed arrow A3 illustrated in FIG. 10). As illustrated in FIG. 10, the PET detector 13c is also caused to move in the gantry by the moving mechanism 20c. The moving mechanism 20c causes the PET detector 13c to move to a position adjacent to the first PET detector 13a in the Z-axis direction of the bore B.

Figure 11:
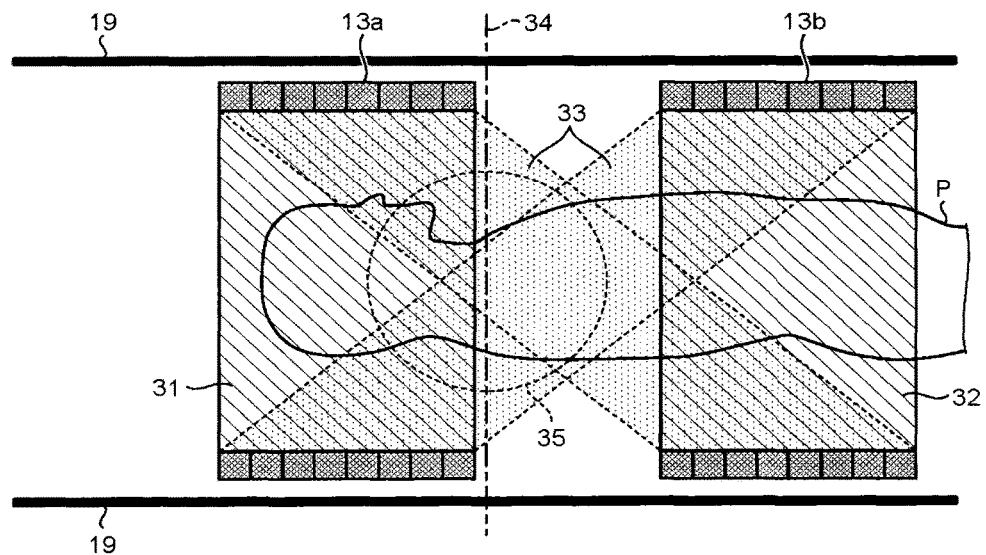
FIG. 11 is a first schematic diagram illustrating an example of effective imaging regions of the PET detector according to the eighth embodiment.
Figure 12:
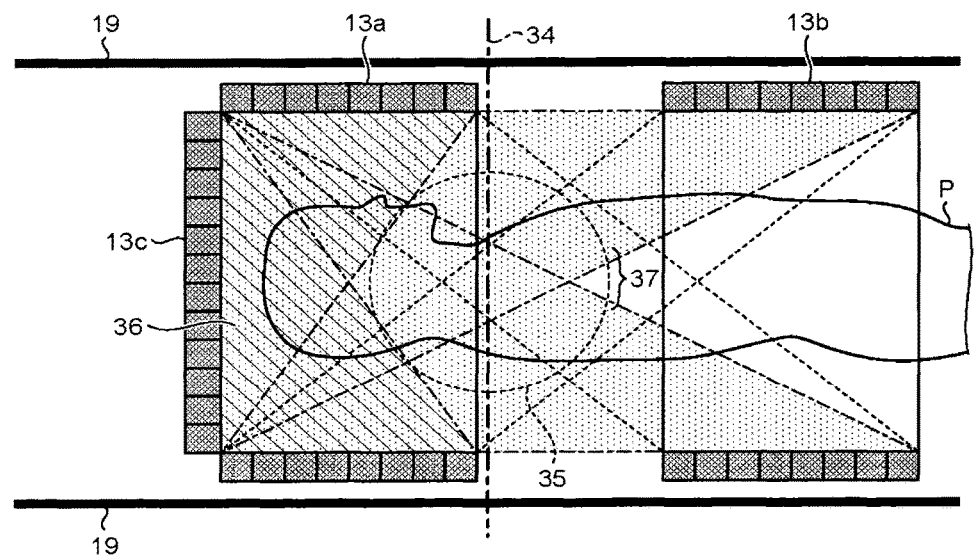
FIG. 12 is a second schematic diagram illustrating an example of the effective imaging regions of the PET detector according to the eighth embodiment.

FIGS. 11 and 12 are schematic diagrams each illustrating an example of effective imaging regions of the PET-MRI apparatus according to the eighth embodiment. In FIGS. 11 and 12, the PET detectors and the bore cover 19 are illustrated but illustration of other components is omitted.

FIG. 11 illustrates an example of effective imaging regions when the PET detector 13c (not illustrated) is distantly separated from the first PET detector 13a. In this case, a region 31 surrounded by the inner circumference of the first PET detector 13a, a region 32 surrounded by the inner circumference of the second PET detector 13b, and a region 33 formed between the inner circumference of the first PET detector 13a and the inner circumference of the second PET detector 13b are the respective effective imaging regions in which PET images can be taken. A straight line 34 illustrated in FIG. 11 indicates the central position in the axial direction of the bore B and a spherical region 35 illustrated in FIG. 11 is the effective imaging region of MR images.

FIG. 12 illustrates the effective imaging regions when the PET detector 13c is placed adjacent to the first PET detector 13a. In this case, in addition to the regions 31 to 33 illustrated in FIG. 11, a region 36 formed between the detection surface of the PET detector 13c and the inner circumference of the first PET detector 13a, and a region 37 formed between the detection surface of the PET detector 13c and the inner circumference of the second PET detector 13b serve as the additional effective imaging regions in which PET images can be taken.

As is obvious also from FIGS. 11 and 12, by placing the PET detector 13c adjacent to the first PET detector 13a, the detection probability of gamma rays emitted from the object P inside the first PET detector 13a can be increased. As a result, the spatial resolution of PET images inside the first PET detector 13a can be increased. FIGS. 11 and 12 each illustrate an example when the head portion of the object P is disposed inside the first PET detector 13a. Similar effect can be obtained also in a case where the foot portion of the object P is disposed there. That is, imaging performed by placing the PET detector 13c adjacent to the first PET detector 13a is preferable when an end portion of the object P is imaged.

In the above-described embodiments, the moving mechanisms of the PET detectors are described. For example, the position of the PET detector caused to move by the moving mechanisms may be detected and the detected position of the PET detector may be displayed on a display unit. In such a case, the computer 10 illustrated in FIG. 1 acquires the amount of movement from the driving device driving the moving mechanism or the position of the PET detector from a position sensor provided to the PET detector, for example. Then, the computer 10 causes the display 12 to display the detected position of the PET detector together with a PET image and an MR image, for example. Meanwhile, the computer 10 may display the position of the magnetic field center together with them.

In the above-described embodiments, the examples are described in which the moving mechanisms are caused to be driven by the driving devices. However, for example, the moving mechanism may be manually operated by an operator.

The dispositions of the PET detectors and the structures of the moving mechanisms described in the above-described embodiments can be arbitrarily combined and implemented. For example, the fourth embodiment illustrated in FIG. 5 may be combined with the sixth embodiment illustrated in FIG. 8 so as to provide the first PET detector 13a disposed on the upper side of the bore B in such a manner that the first PET detector 13a can move outside the static magnetic field magnet 1. In such a case, the bore cover 19 is formed such that it protrudes from the static magnetic field magnet 1 on the side where the couch 2 is not placed, and the first moving mechanism 20a is provided such that it extends in a space formed inside the protruding portion of the bore cover 19.

The respective embodiments described above can lessen effects of interference between the PET detector and the magnetic field on data acquisition.

While the embodiments of the present invention have been described, the embodiments have been presented by way of examples only, and are not intended to limit the scope of the invention. The embodiments described herein may be implemented in other various forms. Furthermore, various omissions, substitutions, and changes of the embodiments described herein may be made without departing from the spirit of the invention. The accompanying claims and their equivalents are intended to cover the embodiments or the modifications as would fall within the scope and spirit of the invention.

What is claimed is:

1. A positron emission tomography (PET)-magnetic resonance imaging (MRI) apparatus, comprising:
    a gantry including:
        a static magnetic field magnet configured to generates a static magnetic field in a bore having an approximately cylindrical shape;
        a gradient coil disposed on an inner circumference side of the static magnetic field magnet and configured to apply a gradient magnetic field to an object disposed in the bore; and
        a radio frequency coil disposed on an inner circumference side of the gradient coil and configured to apply a radio frequency magnetic field to the object;
        a PET detector configured to detect gamma rays emitted from a positron-emitting radionuclide injected into the object; and
        a moving mechanism and control circuitry thereof provided to the gantry and configured to cause, throughout a duration of a magnetic resonance (MR) scan of the object, the PET detector to be positioned along an axial direction of the bore to not overlap an effective imaging region of an MR image.

2. The PET-MRI apparatus according to claim 1, further comprising
    a bore cover configured to cover an inner circumference side of the radio frequency coil, wherein
    the PET detector is disposed between the radio frequency coil and the bore cover.

3. The PET-MRI apparatus according to claim 1, further comprising
    a radio frequency shield disposed between the gradient coil and the radio frequency coil and configured to shield the radio frequency magnetic field generated by the radio frequency coil, wherein
    the PET detector is disposed between the gradient coil and the radio frequency shield.

4. The PET-MRI apparatus according to claim 1, wherein
    the PET detector is a first PET detector and
    the moving mechanism is a first moving mechanism, the PET-MRI apparatus further comprising:
    a couchtop on which the object is placed;
    a couch configured to cause the couchtop to move into the bore with the longitudinal direction of the couchtop being along the axial direction of the bore;
    a second PET detector provided to the couchtop such that the second PET detector is movable in the longitudinal direction of the couchtop; and
    a second moving mechanism configured to cause the second PET detector to move in the longitudinal direction of the couchtop.

5. The PET-MRI apparatus according to claim 1, further comprising:
    a couchtop on which the object is placed; and
    a couch configured to cause the couchtop to move into the bore with the longitudinal direction of the couchtop being along the axial direction of the bore, wherein
    the PET detector is divided into a first PET detector and a second PET detector,
    the first PET detector is disposed around the bore,
    the second PET detector is disposed to the couchtop, and
    the moving mechanism causes the first PET detector and the second PET detector to move independently from each other.

6. The PET-MRI apparatus according to claim 4, further comprising
    a retainer configured to retain the first PET detector such that the first PET detector is movable in the bore, wherein
    the moving mechanism causes the second PET detector to move along the axial direction of the bore in coordination with movement of the first PET detector.

7. The PET-MRI apparatus according to claim 4, wherein the second PET detector has a width larger than the width of the first PET detector in the axial direction of the bore.

8. The PET-MRI apparatus according to claim 1, wherein the PET detector includes
    a first PET detector formed in a ring shape and having a detection surface on an inner circumference of the ring and a second PET detector having a detection surface that is approximately perpendicular to the axial direction of the bore, and the moving mechanism causes the second PET detector to move to a position adjacent to the first PET detector in the axial direction of the bore.

9. The PET-MRI apparatus according to claim 1, further comprising:

a position detection unit configured to detect a position of the PET detector; and a display unit configured to display the position of the PET detector detected by the position detection unit.

10. The PET-MRI apparatus according to claim 1, wherein the PET detector is provided such that the PET detector is capable of moving outside the static magnetic field magnet.

11. The PET-MRI apparatus according to claim 1, wherein the moving mechanism causes the PET detector to additionally move in the up-down direction.

\* \* \* \* \*